United States Patent
Kinjo et al.

(10) Patent No.: US 7,476,545 B2
(45) Date of Patent: Jan. 13, 2009

(54) METHOD OF QUICKLY DETECTING AND/OR ASSAYING ANTIGEN BY FLUORESCENCE CORRELATION SPECTROMETRY

(75) Inventors: Masataka Kinjo, Sapporo (JP); Motohiro Horiuchi, Sapporo (JP); Fumihiko Fujii, Sapporo (JP); Hiroshi Sakata, Sapporo (JP); Mamoru Tamura, Sapporo (JP); Masayoshi Ueno, Obihiro (JP); Takayuki Yanagiya, Obihiro (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 11/633,345

(22) Filed: Dec. 4, 2006

(65) Prior Publication Data

US 2007/0154950 A1 Jul. 5, 2007

Related U.S. Application Data

(63) Continuation-in-part of application No. PCT/JP2005/010043, filed on Jun. 1, 2005.

(30) Foreign Application Priority Data

Jun. 3, 2004 (JP) ............................. 2004-166440

(51) Int. Cl.
*G01N 21/76* (2006.01)
(52) U.S. Cl. ........................ 436/172; 435/7.1; 435/7.92; 435/7.94; 436/164; 436/501; 436/536
(58) Field of Classification Search .................. 435/7.1, 435/7.92–7.95; 436/501, 518, 536, 164, 436/172
See application file for complete search history.

(56) References Cited

U.S. PATENT DOCUMENTS

| | | | |
|---|---|---|---|
| 6,582,903 B1 | 6/2003 | Rigler et al. | |
| 7,045,297 B2 * | 5/2006 | Hajizadeh et al. | ............ 435/7.1 |
| 7,241,569 B2 * | 7/2007 | Rigler et al. | .................... 435/6 |
| 2002/0042121 A1 | 4/2002 | Riesner et al. | |
| 2003/0148374 A1 * | 8/2003 | Kurano et al. | ................ 435/7.1 |
| 2004/0142386 A1 | 7/2004 | Rigler et al. | |

FOREIGN PATENT DOCUMENTS

| | | |
|---|---|---|
| DE | 4301005 | 1/1993 |
| EP | 0679251 | 1/1994 |
| JP | 2001-272404 | 10/2001 |
| JP | 3517241 | 1/2004 |
| JP | 2005-006566 | 1/2005 |
| WO | WO 94/16313 | 7/1994 |
| WO | WO 01/02839 | 1/2001 |
| WO | WO 01/16600 | 3/2001 |
| WO | WO 02/079781 | 10/2002 |
| WO | WO 03/081243 | 10/2003 |
| WO | WO 2004/013610 | 2/2004 |
| WO | WO 2004/035522 | 4/2004 |

OTHER PUBLICATIONS

ABSTRACT: A. Giese, et al., Putting Prions Into Focus: Application Of A Single Molecule Detection To The Diagnosis Of Prion Diseases, Arch Virol. Suppl. (2000) vol. 16, p. 161-171.

* cited by examiner

*Primary Examiner*—Long V Le
*Assistant Examiner*—Gary W Counts
(74) *Attorney, Agent, or Firm*—Frommer Lawrence & Haug LLP; Thomas J. Kowalski; Russell A. Garman

(57) ABSTRACT

The present invention provides a method of quickly and accurately detecting and/or assaying an antigen using fluorescence correlation spectroscopy (FCS), which involves a fluorescence-labeled antibody fragment and a non-fluorescence-labeled intact antibody that form a complex with the antigen. There is a significant difference in diffusion rate between the fluorescence-labeled antibody fragment not bonded to the antigen and the complex formed by the the fluorescence-labeled antibody fragment, the antigen, and the non-fluorescence-labeled intact antibody, and this diffusion rate can be determined using FCS. The antigen can be an antigenic protein, such as an abnormal prion or a harmful protein contained in a food material. According to this method, antigens over a wide scope can be assayed regardless of the shape or molecular weight.

10 Claims, 3 Drawing Sheets

Significant difference in diffusion time (antigen(-))

# US 7,476,545 B2

METHOD OF QUICKLY DETECTING AND/OR ASSAYING ANTIGEN BY FLUORESCENCE CORRELATION SPECTROMETRY

INCORPORATION BY REFERENCE

This application is a continuation-in-part application of international patent application Serial No. PCT/JP2005/010043 filed Jun. 1, 2005, which published as international publication No. WO 2005/119256 on Dec. 15, 2005, which claims priority to Japanese patent application Serial No. JP 2004-166440 filed Jun. 3, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a method of quickly detecting and/or assaying an antigen, whereby an antigen such as an antigenic protein, for example, a pathogenic protein (e.g., an abnormal prion) or a harmful protein contained in a food material is detected and/or assayed quickly by using fluorescence correlation spectroscopy.

BACKGROUND OF THE INVENTION

In recent years, concerns have been raised regarding the presence of harmful proteins, pathogenic proteins, or the like in natural product-derived food materials or feed materials. An example of a harmful protein includes an allergen protein contained in food materials such as buckwheat, wheat, and rice. An example of a pathogenic protein includes an abnormal prion (infectious) contained in materials for edible meat and meat-and-bone meal.

To further illustrate a representative example of a pathogenic protein of recent concern, an abnormal prion is a protein that causes prion disease typified by bovine spongiform encephalopathy (BSE). A normal prion protein is a glyocoprotein that is commonly present in animal brain and on the neural cell membrane surface, and has a molecular weight of approximately thirty-three thousand to thirty-five thousand Daltons(33 to 35 kDa). In contrast, its infectious prion protein form is intracellularly accumulated in the brain (Lait, 76: 571-578, 1996). After entering into an animal body, abnormal prions convert normal prions, which are produced at particular sites in the body, into abnormal prions. This results in the accumulation of the abnormal prions at those particular sites. The accumulation of the abnormal prions in the brain renders the brain spongiform, leading to animal death.

The use of such food materials or feed materials requires detecting and assaying any harmful proteins (e.g., an allergen protein) or pathogenic proteins that are contained in these materials, thereby avoiding the use of the food and feed materials and preventing ingestion of the proteins by humans or animals.

Immunoassay such as ELISA (enzyme-linked immunosorbent assay) or Western blotting (immunoblotting) has here tofore been used to assay natural biological proteins such as prions (abnormal). ELISA is a method performed on a solid phase, wherein an antigen or an antibody is labeled with an enzyme, and the presence of the antibody or the antigen is detected by use of the enzyme activity. For example, ELISA can involve a procedure of binding a Mab 3F4 antibody to a prion immobilized on a microtiter plate and detecting this antibody with a second antibody; the second antibody is coupled to an enzyme which catalyzes a coloring reaction that can be detected (U.S. Pat. No. 4,806,627). Alternatively, Western blotting is a method wherein a protein separated by electrophoresis is immobilized on a hydrophobic membrane, and the protein of interest is detected with an antigen-specific antibody. The detection of an abnormal prion by Western blotting is performed, for instance, by a procedure using a monoclonal anti-prion protein antibody Mab 13A5 (J. Infect. Dis. 154: 518-521, 1986).

However, to detect and assay a prion by a conventional method such as ELISA or Western blotting, the method involves performing in advance, for example, a procedure of digestion and removal of a normal prion from a test sample by treatment with proteinase K. This procedure is for detecting an abnormal prion separately from a normal prion. Western blotting also requires performing electrophoresis. These methods involve complexities and takes much time. Furthermore, in order to achieve the necessary sensitivity, ELISA requires subjecting a sample to denaturation treatment with guanidine thiocyanate after proteinase K treatment. ELISA also requires performing primary denaturation treatment with SDS and a protein concentration procedure by methanol treatment before the deaggregation of the prion protein. In addition, centrifugation must be performed both before the methanol treatment and before the treatment with guanidine thiocyanate. This centrifugation procedure can take much time. In all, these methods involve complicated treatments and therefore present a problem of being unsuitable for testing a large number of samples in a short period of time.

Thus, to improve the problems of ELISA or Western blotting used in the detection and assay of a prion, some other methods have been recently proposed. For example, Japanese Patent Application No. 10-267928 relates to an immuno-PCR method that applies ELISA in detecting an abnormal prion protein with high sensitivity, wherein an anti-prion protein antibody is used and labeled with an arbitrary DNA fragment that is detected by PCR.

Japanese Patent Application No. 2003-130880 relates to a method of immunoassaying an abnormal prion with high sensitivity without performing a time-consuming electrophoresis or centrifugation procedure of the conventional ELISA or Western blotting methods. In this method, a first antibody for inducing an antigen/antibody reaction with an abnormal prion treated with a denaturing agent, or an antigen-binding fragment thereof, is immobilized on magnetic particles and used as an immunoassay reagent. As a result, the method assays the abnormal prion without performing the centrifugation procedure or electrophoresis, and can test a large number of samples in a short time.

Furthermore, Japanese Patent Application No. 2003-215131 relates to a method of analyzing a prion protein by using a mass spectrum, wherein a prion protein in a body fluid sample is allowed to form a covalent bond by reaction with a chemical. Hence, in the presence of a pathogenic prion, at least one additional peak is observed in the mass spectrum.

These methods are modifications of the conventional ELISA or Western blotting methods, although they still must undergo a variety of treatments. Thus, these methods are not necessarily sufficient for conveniently and quickly detecting and assaying an antigenic protein such as a prion. Moreover, these methods are less-than-suitable for automatically or semi-automatically performing treatment steps for detection and assay, and for assaying large amounts of samples.

In contrast, fluorescence correlation spectroscopy (FCS) has been known in recent years as an analysis method that is frequently used particularly in the analysis of molecules derived from organisms. This method can detect and assay, in almost real time, the physical parameters of protein molecules such as number, size, or shape, without undergoing a step of physically separating the sample (Chem. Phys., 4, 390-401, 1974; Biopolymers, 13, 1-27, 1974; Physical Rev. A, 10: 1938-1945,1974; in Topics in Fluorescence Spectroscopy, 1, pp. 337-378, Plenum Press, New York and London, 1991; and R. Rigler, E. S. Elson (Eds.), Fluorescence Correlation Spectroscopy. Theory and Applications, Springer, Berlin, 2001). FCS is practiced by capturing, within an exceedingly small region, the Brownian motions of fluorescence-labeled target molecules in a medium by a laser confocal scanning microscope system. This provides an analysis of the diffusion time from the fluctuation of fluorescence intensity and an assay of the physical parameters of the target molecules (the number and size of the molecules). Thus, FCS serves as an effective means in specifically detecting intermolecular interaction with high sensitivity.

The feature of FCS used in the detection and assay of a protein, or the like, contained in a biological sample is that the concentrations or intermolecular interactions of fluorescence-labeled target molecules contained in a solution can be monitored in almost real time without undergoing a physical separation step. Therefore, a detection system using FCS can avoid a complicated Bound/Free separation step necessary for conventional analysis means (e.g., ELISA) and predominantly used in biomolecule detection systems. This technique can assay large amounts of samples with high sensitivity in a short time and is also suitable for automatic assay.

To detect an antigenic protein or the like by using FCS, a fluorescence-labeled antibody molecule is used, and an antigen/antibody reaction occurs between the fluorescence-labeled antibody and the antigenic protein. Analysis is performed by utilizing the difference in diffusion rate that occurs due to the shapes and molecular weights of the fluorescence-labeled antibody and the fluorescence-labeled antibody/antigenic protein complex. In this context, the diffusion rate (diffusion constant or D) refers to an area where molecules are freely diffused per unit time. The diffusion time (DT or τD) refers to time required for molecules to pass through a determined focal region that depends on the apparatus.

Thus, FCS provides an accurate assay of an antigenic protein or the like in a sample by using the difference in diffusion rates between the labeled antibody and the antigen/antibody complex formed by the labeled antibody and the antigenic protein. FCS could previously detect only the exceedingly limited type of an antigenic protein or the like due to this requirement. Conventional means for solving this problem comprised applying a variety of modifications to an antigen/antibody complex in consideration of the shapes and molecular weights of the antigen and the antibody and providing a significant difference in diffusion rate (Japanese Patent Application No. 2001-272404 and Japanese Patent No. 3517241). However, even if these methods were used, the applicability of FCS was limited regarding which objects could be detected.

Patent Document 1: Japanese Patent Application No. 10-267928
Patent Document 2: Japanese Laid-Open Patent Application No. 2001-272404
Patent Document 3: Japanese Laid-Open Patent Application No. 2003-130880
Patent Document 4: Japanese Laid-Open Patent Application No. 2003-215131
Patent Document 5: Japanese Patent No. 3517241
Non-Patent Document 1: J. Infect. Dis. 154: 518-521, 1986
Non-Patent Document 2: Chem. Phys., 4, 390-401, 1974
Non-Patent Document 3: Biopolymers, 13, 1-27, 1974
Non-Patent Document 4: Physical Rev. A, 10: 1938-1945, 1974
Non-Patent Document 5: in Topics in Fluorescence Spectroscopy, 1, pp. 337-378, Plenum Press, New York and London, 1991
Non-Patent Document 6: R. Rigler, E. S. Elson (Eds.), Fluorescence Correlation Spectroscopy, Theory and Applications, Springer, Berlin, Citation or identification of any document in this application is not an admission that such document is available as prior art to the present invention

SUMMARY OF THE INVENTION

An object of the present invention is to provide a quick and convenient method of detecting and/or assaying an antigen or an antigenic protein such as a pathogenic protein (e.g., an abnormal prion) or a harmful protein contained in a food material.

During diligent studies to attain the above object, the present inventors have focused their attention on fluorescence correlation spectroscopy (FCS). Recently, FCS has been known as a method that is frequently used in the analysis and the like of molecules derived from organisms and that can detect and assay, in almost real time, the physical parameters of protein molecules, such as number, size, or shape without undergoing a physical separation step. The present inventors learned that fluorescently-labeling the antigen molecule to be detected, and using a fluorescence-labeled antibody fragment and a non-fluorescence-labeled intact antibody that binds together via the antigen in the fluorescence labeling, can allow a significant difference in diffusion rate to arise between the fluorescence-labeled antibody fragment not bonded to the antigen and the complex formed by the fluorescence-labeled antibody fragment, the antigen, and the non-fluorescence-labeled intact antibody. The present inventors discovered that, according to this method, a wide scope of antigens can be detected and assayed using FCS, including antigens that have relatively low molecular weight such as an antigenic protein, independent from the shape or molecular weight of the antigen. Based on these findings, the present invention has been completed.

Specifically, the present invention may comprise a method of detecting and/or assaying an antigen, such as an antigenic protein, by using a fluorescence-labeled antibody fragment targeted to an epitope of the antigen and a non-fluorescence-labeled intact antibody targeted to another epitope of the antigen which together forms an antigen/antibody complex among the antigen, the fluorescence-labeled antibody fragment, and the non-fluorescence-labeled intact antibody. The method may further comprise detecting and analyzing the formed antigen/antibody complex by fluorescence correlation spectroscopy. The detection and/or assay method of the present invention can be applied widely to the detection and/or assay of an antigenic protein, for example, a pathogenic protein (e.g., an abnormal prion) or a harmful protein contained in a food material, whereby the antigenic protein can be detected and/or assayed quickly and accurately by a simple procedure.

The function of the present invention will be further described. The present invention may comprise (i) mixing a fluorescence-labeled antibody fragment and an intact antibody (or a mixture thereof, i.e., an antigen detection reagent provided by the present invention) with an antigen such as an antigenic protein (e.g., a pathogenic protein such as an abnormal prion or a harmful protein such as an allergen protein), in which the antibody fragment and intact antibody each targets a different epitope (antigenic determinant) of the antigen; (ii) performing antigen/antibody reaction among the antibody fragment, the intact antibody, and the antigen; and (iii) assaying the mixture by FCS. In the presence of an antigen, such as an antigenic protein, in a detection and/or assay sample, the fluorescence-labeled antibody fragment and the non-fluorescence-labeled intact antibody may form a complex via the antigen (FIG. 1).

Specifically, the present invention may relate to: (1) a method of quickly detecting and/or assaying an antigen by fluorescence correlation spectroscopy, comprising the use of a fluorescence-labeled antibody fragment targeted to an epitope of an antigen and a non-fluorescence-labeled intact antibody targeted to another epitope of the antigen to form an antigen/antibody complex among the antigen, the fluorescence-labeled antibody fragment, and the non-fluorescence-labeled intact antibody, and detecting and analyzing the formed antigen/antibody complex by fluorescence correlation spectroscopy; (2) the method of quickly detecting and/or assaying an antigen by fluorescence correlation spectroscopy according to (1), wherein the antigen is an antigenic protein; (3) the method of quickly detecting and/or assaying an antigen by fluorescence correlation spectroscopy according to (1) or (2), wherein the detection and analysis of the formed antigen/antibody complex by fluorescence correlation spectroscopy are a detection and an analysis of an antigen utilizing discrimination on the basis of a difference in diffusion rate between the fluorescence-labeled antibody fragment and the formed antigen/antibody complex that has been labeled; (4) the method of quickly detecting and/or assaying an antigen by fluorescence correlation spectroscopy according to any one of (1) to (3), wherein the quick detection and/or assay of an antigen are detection and/or assay of the presence, concentration, size, or shape of an antigen on the basis of detection and analysis of the formed antigen/antibody complex by fluorescence correlation spectroscopy; and (5) the method of quickly detecting and/or assaying an antigen by fluorescence correlation spectroscopy according to any one of (1) to (4), wherein the fluorescence-labeled antibody fragment targeted to an epitope of an antigen is prepared from a monoclonal antibody prepared with an antigen as an immunogen, and the non-fluorescence-labeled intact antibody targeted to another epitope of an antigenic protein is a monoclonal antibody prepared with an antigen as an immunogen.

The present invention may also relate to: (6) a method of quickly detecting and/or assaying an antigen by fluorescence correlation spectroscopy, comprising the addition of a fluorescence-labeled antibody fragment targeted to an epitope of an antigen and a non-fluorescence-labeled intact antibody targeted to another epitope of the antigen to a test sample, performing antigen/antibody reaction thereamong, and detecting and analyzing an antigen/antibody complex formed among the antigen, the fluorescence-labeled antibody fragment, and the non-fluorescence-labeled intact antibody by fluorescence correlation spectroscopy; (7) the method of quickly detecting and/or assaying an antigen by fluorescence correlation spectroscopy according to (6), wherein the antigen is an antigenic protein; (8) the method of quickly detecting and/or assaying an antigen by fluorescence correlation spectroscopy according to (6) or (7), wherein the detection and/or assay of an antigen by fluorescence correlation spectroscopy are performed without undergoing a step of physically separating the antigen contained in the test sample; (9) the method of quickly detecting and/or assaying an antigen by fluorescence correlation spectroscopy according to any one of (6) to (8), wherein the step of adding a fluorescence-labeled antibody fragment targeted to an epitope of the antigen and a non-fluorescence-labeled intact antibody targeted to another epitope of the antigen to a test sample, the step of performing antigen/antibody reaction among the test sample, the fluorescence-labeled antibody fragment, and the non-fluorescence-labeled intact antibody, and the step of detecting and analyzing the test sample that has undergone the antigen/antibody reaction by fluorescence correlation spectroscopy are performed automatically or semi-automatically; and (10) the method of quickly detecting and/or assaying an antigen by fluorescence correlation spectroscopy according to any one of (6) to (9), wherein the test sample is a biological protein ample, and the antigen is a pathogenic protein antigen.

The present invention may further relate to: (11) the method of quickly detecting and/or assaying an antigen by fluorescence correlation spectroscopy according to (10), wherein the pathogenic protein antigen is an abnormal prion; (12) the method of quickly detecting and/or assaying an antigen by fluorescence correlation spectroscopy according to any one of (6) to (9), wherein the test sample is a food material, and the antigen is a harmful protein antigen contained in the food material; (13) a detection reagent for quickly detecting and/or assaying an antigen by fluorescence correlation spectroscopy, comprising a fluorescence-labeled antibody fragment targeted to an epitope of an antigen to be detected and/or assayed and a non-fluorescence-labeled intact antibody targeted to another epitope of an antigen to be detected and/or assayed; and (14) a kit for quickly detecting and/or assaying an antigen by fluorescence correlation spectroscopy, comprising the detection reagent according to (12).

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawing, in which.

DETAILED DESCRIPTION OF THE INVENTION

Figure 1:
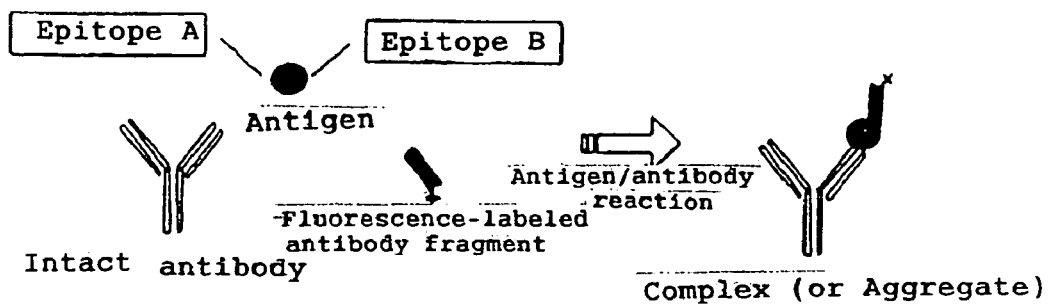
FIG. 1 is a diagram showing the outline of a method of quickly detecting and/or assaying an antigen-by FCS of the present invention.

A method of quickly detecting and/or assaying an antigen by fluorescence correlation spectroscopy (FCS) as disclosed in the present invention comprises using a fluorescence-labeled antibody fragment targeted to an epitope of the antigen and a non-fluorescence-labeled intact antibody targeted to another epitope of the antigen in order to form an antigen/antibody complex among the antigen, the fluorescence-labeled antibody fragment, and the non-fluorescence-labeled intact antibody, and detecting and analyzing the formed antigen/antibody complex by FCS.

Specifically, to practice the present invention, the method of quickly detecting and/or assaying an antigen is performed by (i) adding a fluorescence-labeled antibody fragment targeted to an epitope of the antigen and a non-fluorescence-labeled intact antibody targeted to another epitope of the antigen to a test sample; (ii) performing antigen/antibody reaction by mixing the sample supplemented with the antibody; and (iii) detecting and analyzing an antigen/antibody complex formed among the antigen, the fluorescence-labeled antibody fragment, and the non-fluorescence-labeled intact antibody by FCS to thereby quickly detect and/or assay the presence, size, concentration, or the like of the antigen in the sample. A treatment procedure in the detection and/or assay by FCS of the present invention is performed by a procedure of merely adding and mixing the sample to a detection reagent comprising the fluorescence-labeled antibody fragment and the non-fluorescence-labeled intact antibody, without undergoing a step of physically separating the antigen contained in the test sample. Therefore, the step of detecting and assaying the antigen can be performed automatically or semi-automatically.

In the present invention, to prepare a fluorescence-labeled antibody fragment and a non-fluorescence-labeled intact antibody used as a detection reagent, antibodies specifically binding to the antigen are prepared. The antibodies specifically binding to an antigen that are used in the present invention can include polyclonal antibodies and monoclonal antibodies, preferably the monoclonal antibodies in terms of their specificity, and preferably IgG class monoclonal antibodies. To prepare such antibodies against the antigen, the antigen to be detected is first purified and obtained. The antigen can be prepared by isolation and purification from a donor source using purification means known in the art. Alternatively, if the antigen is an antigenic protein having its amino acid sequence known in the art, the antigenic protein can be obtained by a genetic engineering approach whereby microorganisms, animal cells, or the like are used and allowed to produce the antigenic protein, followed by purification. The antigenic protein can be prepared, when possible, by a chemical peptide synthesis method. The chemical peptide synthesis can adopt synthesis means known in the art. Examples thereof include azide, acid chloride, acid anhydride, mixed anhydride, DCC, active ester, carboimidazole, and oxidation-reduction methods.

To prepare antibodies against the antigen, animals or plants are sensitized to the antigen by use of a routine protocol to prepare the antibodies. Any method such as a hybridoma method (Nature 256, 495-497, 1975), trioma method, human B cell hybridoma method (Immunology Today 4, 72, 1983), and EBV-hybridoma method (MONOCLONAL ANTIBODIES AND CANCER THERAPY, pp. 77-96, Alan R. Liss, Inc., 1985), which provide antibodies produced by cultures of continuous cell lines, can be used, for example, in monoclonal antibody preparation.

To prepare monoclonal antibodies against an antigen such as an antigenic protein, for example, mammals such as rat, mice, or rabbits are sensitized by administering the antigenic protein as an antigen to them. An adjuvant such as a Freund's complete adjuvant (FCA) or a Freund's incomplete adjuvant (FIA) can be used, if necessary. The immunization is performed mainly by intravenous, hypodermic, or intraperitoneal injection. Moreover, a time interval between immunizations is not particularly limited, and 1 to 10 immunizations are performed at several-day to several-week intervals. One to sixty days after the final immunization day, antibody-producing cells are collected. The antibody-producing cells include spleen cells, lymph node cells, and peripheral blood cells. To obtain hybridomas, cell fusion is performed between the antibody-producing cells and myeloma cells. Generally obtainable cell lines can be used as the myeloma cells to be fused with the antibody-producing cells. The cell lines used have drug selectivity and possess the property of being inviable in the unfused form in a HAT selective medium (which contains hypoxanthine, aminopterin, and thymidine) but viable therein only in the form fused with the antibody-producing cells.

Hybridomas of interest are selected from the cells after the cell fusion treatment. A usual cell culture method or ascites formation method can be adopted as a method of collecting monoclonal antibodies from the established hybridomas. When the method of collecting antibodies requires antibody purification, the antibodies can be purified by appropriately selecting methods known in the art such as ammonium sulfate precipitation, ion-exchange chromatography, gel filtration, and affinity chromatography, or combining these methods. In the present invention, in addition to the antibodies thus prepared, commercially available already-prepared antibodies, if any, can be used as an antibody against the antigenic protein used in the present invention.

In the method of quickly detecting and/or assaying an antigen of the present invention, a fluorescence-labeled antibody fragment prepared from the antigen is used as a detection reagent for performing antigen/antibody reaction with the antigen and detecting the antigen. In the present invention, an antibody that binds to an epitope of the antigen different from that for the non-fluorescence-labeled intact antibody used in the present invention is selected as an antibody used in the preparation of the fluorescence-labeled antibody fragment. To prepare the fluorescence-labeled antibody fragment, a intact antibody against the antigen is fragmented with an enzyme such as pepsin and papain and converted to a monomer by reduction with, for example, 2-mercaptomethylamine or 2-mercaptoethanol, followed by labeling to thereby prepare the fluorescence-labeled antibody fragment. A fluorescent dye is used in the labeling. A fluorescent dye such as fluorescein isothiocyanate (FITC) and Alexa 532 is used.

In the method of quickly detecting and/or assaying an antigen of the resent invention, the fluorescence-labeled antibody fragment and the non-fluorescence-labeled intact antibody as a detection reagent are added and mixed to a test sample. The test sample that has undergone antigen/antibody reaction is subjected to the detection and/or assay of the antigen by FCS (fluorescence correlation spectroscopy). FCS is a method whereby the Brownian motions of fluorescent molecules in a solution are used to obtain the physical parameters of the molecules such as "size" or "number." The feature of FCS is that the concentrations or intermolecular interactions of fluorescent molecules contained in a solution can be monitored in almost real time without undergoing a physical separation step. Therefore, a detection system using FCS can avoid a complicated Bound/Free separation step necessary for conventional biomolecule detection systems (e.g., ELISA) performed predominantly. Thus, large amounts of samples can be assayed automatically with high sensitivity in a short time. A variety of FCS techniques are known, and any method can be used in the present invention unless it hinders the detection and assay of an object to be detected and assayed by the present invention (Protein, Nucleic Acid and Enzyme, Vol. 44, No. 9, 1431-1438, 1999; Bio Industry, April issue, p. 52-59, 2003; Japanese Laid-Open Patent Application No. 2001-272404; and Japanese Patent No. 3517241).

Figure 4:
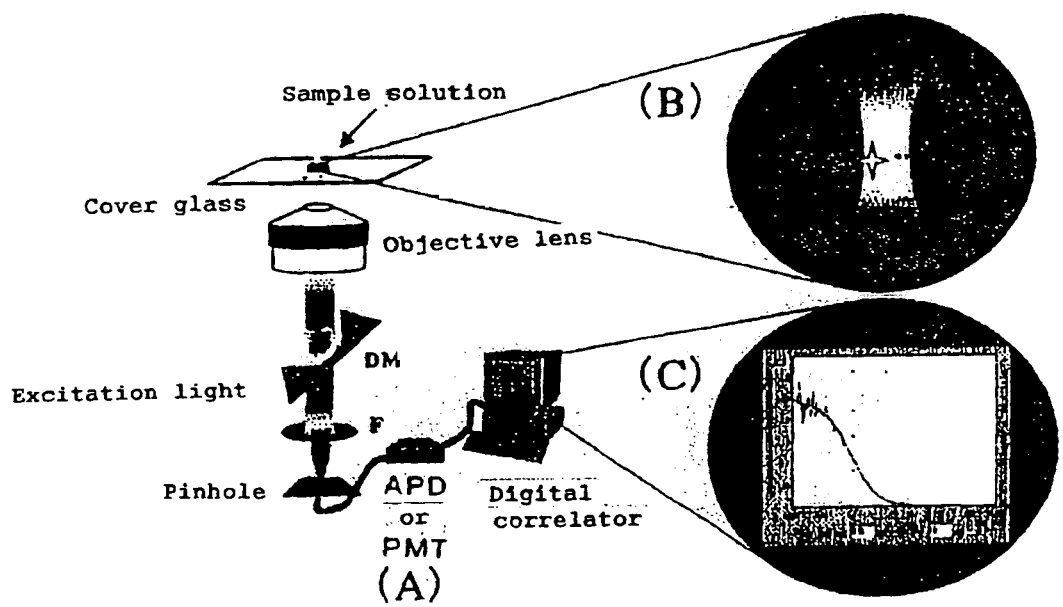
FIG. 4 is a diagram showing the outline of an apparatus for FCS assay used in the present invention.

The basic structure of an apparatus used in the detection and assay by FCS is shown in FIG. 4. To briefly explain it with reference to the figure, FIG. 4(A) shows a schematic view of an FCS (fluorescence correlation spectroscopy) apparatus. Excitation light from a laser is erected to a sample solution on a cover glass via a dichroic mirror (DM) and an objective lens. Emitted fluorescence passes through a long pass or band pass filter (F) and is directed to an avalanche photodiode detector (APD) or a photomultiplier (PMT) after the background light outside the confocal surface is removed by a confocal pinhole. The signal is further analyzed in a digital correlator. FIG. 4(B) shows a magnified schematic view of the observation region. It shows the state where a fluorescent molecule moving in Brownian motion passes through the confocal region narrowed down to the limit by the objective lens. FIG. 4(C) shows a correlation curve after fluorescence correlation analysis. The physical parameters of molecules such as "number" or "size" are obtained by analyzing the observed fluctuation of fluorescence intensity by use of formulas.

In the assay by FCS, fluorescence from the exceedingly small region (approximately 400 nm in diameter, approximately 2 μm in axis length, less than $10^{-16}$ l in volume) of the sample solution is detected by using a confocal optical system (FIG. 4). In the Examples of the present invention, MF20 manufactured by Olympus Corp. was used as an apparatus for FCS assay. The assay was practiced by a scheme wherein three 30-second measurements were performed at wavelengths of 543 and 633 nm.

In the assay by FCS, fluorescent molecules go into and out of an observation region according to their Brownian motions because the observation region is an open system. Consequently, the number of the molecules in the observation region varies around a certain value, causing the fluctuation of the number. The fluctuation of fluorescence intensity attributed to this fluctuation of the number is observed (Protein, Nucleic Acid and Enzyme, Vol. 44, No. 9, 1431-1438, 1999).

The observed fluctuation of fluorescence intensity is analyzed by use of formulas (1) to (4) described below to thereby obtain the physical parameters of molecules such as "number" or "size." Specifically, to draw information from the signal of fluctuation, an autocorrelation function is used. The autocorrelation function used in FCS is represented by the formula (1).

Formula 1

$$C(\tau) = 1 + \frac{1}{N}\left[\frac{1}{1+\tau/\tau_D}\right]\left[\frac{1}{1+(1/s)^2(\tau/\tau_D)}\right]^{1/2}$$

In this context, s=z/w, a ratio of the semimajor axis (z) of the observation region to the radius (w) thereof; $\tau_D$ is called diffusion time (or correlation time) and represents average time when the fluorescent molecules pass through the observation region by diffusion; and N represents the average number of the molecules present in the observation region within a fixed time.

The analysis of the fluctuation by the formula (1) gives a curve as shown in FIG. 4 (C), from which the diffusion time $\tau_D$ showing the "mobility" of the molecules and the "number" N of the molecules are obtained. The correlation curve shifts to the right with increases in molecular size, for example, as a result of association of the fluorescent molecules with other molecules, whereas it shifts to the left with decreases in molecular size, for example, as a result of dissociation. The diffusion time $\tau_D$ obtained by the formula (1) stands in the relationship represented by the formula (2) with the diffusion constant D.

$$\tau_D = w^2/4D \qquad \text{Formula 2}$$

Furthermore, the diffusion constant D stands in the relationship represented by the formula (3) with the radius r of the molecule according to the Einstein-Stokes equation based on the assumption that molecules are spherical in shape.

Formula 3

$$D = \frac{\kappa_D T}{6\pi\eta\tau}$$

In this context, $\kappa_B$, T, and η represent the Boltzmann constant, the absolute temperature, and the viscosity of a solvent, respectively. Thus, the diffusion time $\tau_D$ can be linked as shown in the formula (4) to the radius r of the molecule corresponding to the "size" of the molecule according to the formulas (2) and (3).

$$\tau_D \propto 1/D \propto r \qquad \text{Formula 4}$$

As described above, the "number" and "size" of the molecules present in the observation region can be obtained by analyzing the fluctuation of fluorescence intensity by use of the formulas (1) and (4). Detailed explanation about the fluctuation and the autocorrelation function are described in texts (T. Musha, "World of Fluctuation" Kodansha Bluebacks series, Kodansha Ltd., 1980; D. Eisenberg, et al., "Physical Chemistry With Applications To The Life Sciences", the second volume, Baifukan Co., Ltd., p. 596-600, 1988; and M. Hino, "Spectrum Analysis", Asakura Publishing Co., Ltd., p. 25-39, 1977).

Procedures in the detection and/or assay of an antigenic protein by FCS of the present invention and time required therefor are indicated in comparison to those in a method of detecting and/or assaying an antigenic protein by using a conventional ELISA method.

(1) Comparison of Procedures (Comparison of Convenience)

Procedures at each step in the Method of quickly detecting and/or assaying an antigenic protein by FCS of the present invention are shown in Table 1.

TABLE 1

| Step | Method using ELISA | Present method |
|---|---|---|
| Sample treatment step | Immobilization of samples onto plate (antigen/antibody reaction) Washing of non-specifically adsorbed samples and liberated samples (×3) | Labeling of samples with reagent of the present invention (antigen/antibody reaction) |
| Signal amplification step | Immobilization of enzyme-labeled antibodies onto immobilized samples (antigen/antibody reaction) Washing of non-specifically adsorbed reagents (×5) Dispense of substrate-coloring solution (enzyme reaction) Dispense of reaction stop solution (inhibition of enzyme reaction) | — |
| Analysis step | Signal assay with plate reader | Signal analysis by FCS |

(2) Comparison of Time Required (Comparison of Quickness)

Time required for each step in the method of quickly detecting and/or assaying an antigenic protein by FCS of the present invention is shown in Table 2.

TABLE 2

| Step | Method using ELISA | Present method |
|---|---|---|
| Sample treatment step | Immobilization of samples onto plate 75 minutes Washing of non-specifically adsorbed samples and liberated samples 1 minute | Labeling of samples with reagent of the present invention 75 minutes |
| Signal amplification step | Immobilization of enzyme-labeled antibodies onto immobilized samples 60 minutes Washing of non-specifically adsorbed reagents 1 minute Substrate coloring 30 minutes | — |
| Analysis step | Signal assay with plate reader 2 minutes (96 samples) | Signal analysis by FCS 20 minutes (10-sec measurement/sample × 96 samples) |
| Total | 169 minutes | 95 minutes |

Regarding industrial applicability, the present invention describes a method of detecting and/or assaying an antigen by fluorescence correlation spectroscopy (FCS) that can detect and assay an antigen independently of the shape or molecular weight of the antigen. This method is applicable to antigens over a wide scope, including those with a relatively small molecular weight such as an antigenic protein (a pathogenic protein such as an abnormal prion, or a harmful protein) contained in a food material. Moreover, the detection and/or assay method of the present invention performs the detection and/or assay by FCS. Therefore, it can detect and assay the physical parameters of antigen molecules to be detected such as number, size, or shape in almost real time without undergoing a step of physically separating a sample, and can quickly and accurately detect and/or assay an antigen by a simple procedure.

Furthermore, in the method of the present invention, which performs the detection and/or assay by FCS, a treatment procedure for the detection and assay by FCS is performed by a procedure of merely mixing a test sample (which contains an antigen) to a detection reagent, comprised of a fluorescence-labeled antibody fragment and a non-fluorescence-labeled intact antibody, and performing an antigen/antibody reaction. In addition, the assay results can be monitored in almost real time. Therefore, the method of the present invention is suitable for automatically or semi-automatically performing procedures from the mixing and reaction of the detection reagent with the test sample to the indication of the assay results. Moreover, the method of the present invention comprises a smaller number of steps associated with the analysis procedure than that in methods such as ELISA and Western blotting conventionally used in the assay of an antigenic protein such as a prion, and can assay several microliters to several dozen microliters of a sample. Therefore, it can economically assay large amounts of test samples. Thus, the method of the present invention can be expected to be utilized as practical assay means of an antigenic protein.

The invention will now be further described by way of the following non-limiting examples which further illustrate the invention, and are not intended, nor should they be interpreted to, limit the scope of the invention.

EXAMPLES

Example 1

Influence of a Non-fluorescence-labeled Intact Antibody on Diffusion Rate (1) Materials:
Alexa Fluor 647 (Zenon One Mouse IgG1 Labeling Kit)
Fab 647 (Zenon One IgG1 Labeling Reagent)
Antibody (indicated by Ab in FIG. 2) (Zenon One Blocking Reagent (mouse IgG))

(2) Apparatus for FCS Assay:

MF-20 (intermolecular interaction analysis system: Olympus Corp.)

(3) Procedures:

A solution of 10 nM Fab 647 (mouse IgG antibody) alone and a Fab 647 mixture obtained by mixing Fab 647 with 100 nM intact antibody were applied to a 384-well plate (Olympus) blocked with N101 (NOF Corp.), followed by assay with MF20 (Olympus). The assay was performed by 30 sec.×three measurements at a laser power set to 100 μW. The processing software in MF20 was used to derive each parameter including diffusion time.

Figure 2:
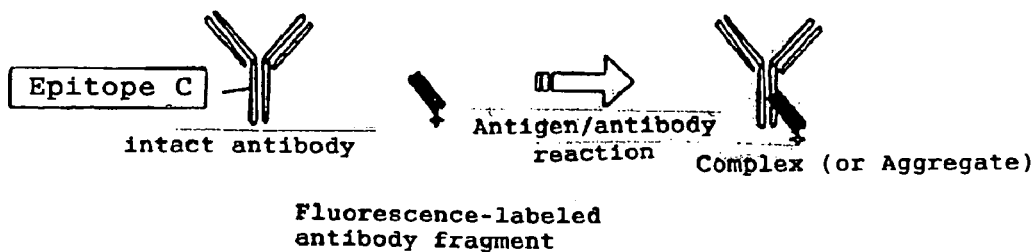
FIG. 2 is a diagram showing the outline of a test on a difference in diffusion rate between a fluorescence-labeled antibody fragment alone and a complex of the fluorescence-labeled antibody fragment and a intact antibody in order to demonstrate the function of the method of quickly detecting and/or assaying an antigen by FCS of the present invention.
Figure 3:
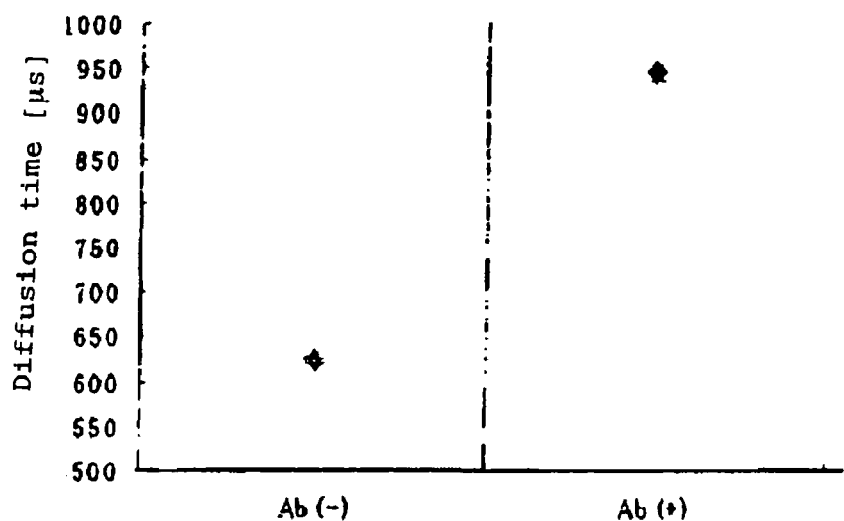
FIG. 3 is a diagram showing a result of the test on a difference in diffusion rate between a fluorescence-labeled antibody fragment alone and a complex of the fluorescence-labeled antibody fragment and a intact antibody in order to demonstrate the function of the method of quickly detecting and/or assaying an antigen by FCS of the present invention.

To test how a non-fluorescence-labeled intact antibody can influence the diffusion rate in the Brownian motion of an antigen/antibody complex molecule, an intact antibody and a labeled antibody fragment directly recognizing it were used to perform FCS assay without the antigen located in the middle of the complex (FIG. 2). As a result of the assay, a significant difference was obtained between the diffusion rate of the labeled antibody fragment alone and the diffusion rate of a labeled antibody fragment/antibody complex (FIG. 3). Namely, as a result of performing antigen/antibody reaction between the fluorescence-labeled antibody fragment, which recognized the Fc domain (FIG. 2, Epitope C) of the non-fluorescence-labeled intact antibody (FIG. 3, Ab), and the non-fluorescence-labeled intact antibody, followed by FCS, as shown in FIG. 3, the diffusion time of the labeled antibody fragment alone (Ab(−)) and the diffusion time of the complex (Ab(+), the fragment and the intact antibody) are, theoretically, approximately 600 μs and 900 μs, respectively. Their measurement values were also approximately 600 μs and 950 μs, respectively, indicating a significant difference in diffusion rate between the labeled antibody fragment alone and the labeled antibody fragment/antibody complex.

These results indicate that when a complex is formed among the fluorescence-labeled antibody fragment, the antigen, and the non-fluorescence-labeled intact antibody wherein antigen is present in the middle of the antigen/antibody complex, a significant difference arises in between the diffusion rate of the fluorescence-labeled molecule of the fragment and the diffusion rate of the fluorescence-labeled molecule of the complex. Thus, it was shown that the use of this combination allows for the detection of an antigen such as an antigenic protein by FCS assay, independently from the molecular weight of the antigen.

Example 2

Detection and Assay of Antigen (Antigenic Protein) using FCS (1) Apparatus

FCS apparatus

Intermolecular interaction analysis system (MF-20, manufactured by Olympus Corp.)

(2) Materials

Preparation of fluorescence-labeled antibody fragment

Figure 5:
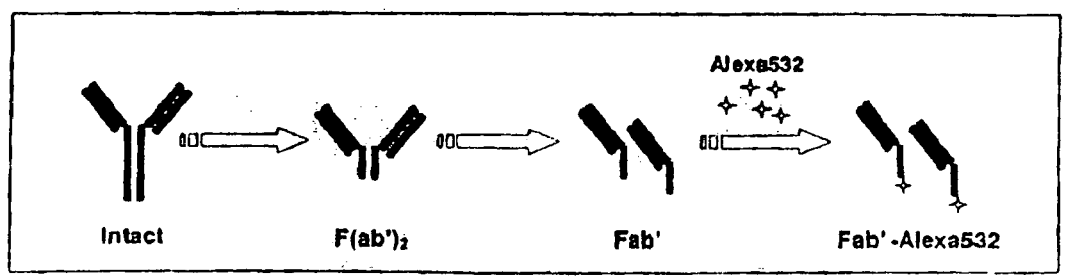
FIG. 5 is a diagram showing the outline of preparation of a fluorescence-labeled antibody fragment used in the method of quickly detecting and/or assaying an antigen by FCS of the present invention.

In this Example, the fluorescence-labeled antibody fragment (Fab'-Alexa 532) of an anti-prion antibody was taken as an example. The outline of preparation of Fab'-Alexa 532 is shown in FIG. 5. An anti-PrP antibody solution was equilibrated with a citric acid solution (pH 6.3) by use of a PD-10 column (Pharmacia) and then supplemented (37° C., approximately 30 minutes) with pepsin (1% (w/w)) to prepare F(ab')$_2$. The degree of the digestion was confirmed by HPLC (column: G300SWXL). Then, the fragment was purified by FPLC (column: Superdex 200 (16/60)) using 0.1 M phosphate buffer solution (pH6.3), then concentrated, and stored. It was further reduced (37° C., approximately 1.5 hours) by the addition of 2-mercaptomethylamine (0.01 M) to prepare Fab'.

The degree of reduction was confirmed by HPLC (column: G300SWXL). The solution was equilibrated with a citric acid solution (pH 3.5) by use of a PD-10 column (Pharmacia), then immediately supplemented with 2 equivalents of Alexa 532 maleimide (Molecular Probe), and left overnight at 4° C. to perform coupling. Then, the resulting fragment was purified by FPLC (column: Superdex 200 (16/60)) using 0.05 M phosphate buffer solution (pH 7.8, 0.05% NH3) and cryopreserved at −80° C. Two types of anti-PrP antibodies (one thus fragmented and labeled, the other used as an intact antibody) and recombinant bovine PrP (antigen) both were provided by FUJIREBIO INC.

Experimental Procedures of Detection and Assay of Antigenic Protein

The Fab'-Alexa 532 (fluorescence-labeled antibody fragment) (6.86E-10M), the prion protein (antigenic protein) (6.12E-8M), and the intact antibody (anti-bovine recombinant prion antibody) (8.76E-7M) were added in this order to a 384-well plate (Olympus Corp.) blocked with N101 (NOF Corp.) and well mixed with a pipette. The plate was left at 37° C. for 1 hour, followed by assay with MF20 (apparatus for FCS assay; Olympus Corp). The assay was performed by three 30-second measurements at a laser power set to 150 μW. The processing software in MF20 was used to derive each parameter including diffusion time.

Figure 6:
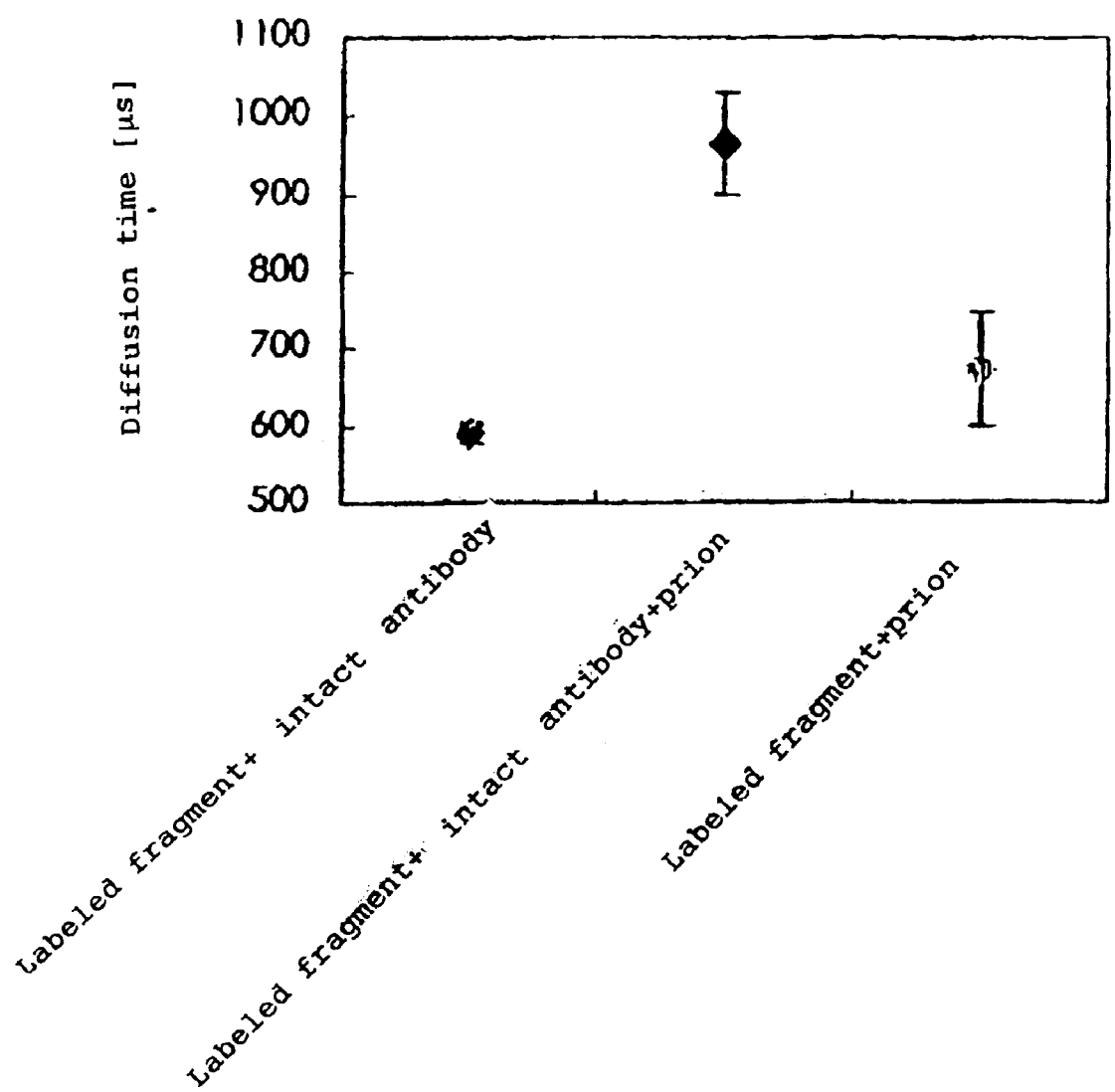
FIG. 6 is a diagram showing a result of using a fluorescence-labeled antibody fragment and a intact antibody to test a difference in diffusion time depending on the formation of a complex of the antibody and an antigenic protein in the Examples of the present invention.

The experimental results are shown in FIG. 6. In this Example, the molecular weight of the prion protein is approximately 30 kDa, and therefore, a significant difference in diffusion time might not arise if the intact antibody is not used. Specifically, the theoretical diffusion times of the fluorescence-labeled antibody fragment and a complex (fluorescence-labeled antibody fragment+prion protein) are approximately 600 μs and 650 μs, respectively. In the experiment as well, the diffusion times of the fluorescence-labeled antibody fragment and the complex (fluorescence-labeled antibody fragment+prion protein) were approximately 600 μs and 650 μs, respectively, indicating no significant difference (FIG. 6). On the other hand, the theoretical diffusion times of the fluorescence-labeled antibody fragment and a complex (fluorescence-labeled antibody fragment+intact antibody+prion protein) are approximately 600 μs and 900 μs, respectively, and are significantly different. In the experiment as well, the diffusion times of the fluorescence-labeled antibody fragment and the complex were approximately 600 μs and 950 μs, respectively, close to the theoretical values, indicating a significant difference (FIG. 6). Thus, this Example demonstrated that an antigen with a small molecular weight that cannot be detected unless the method of the present invention is used can be detected by using the present method.

The invention is further described by the following numbered paragraphs:

1. A method of quickly detecting and/or assaying an antigen by fluorescence correlation spectroscopy, comprising: (i) using a fluorescence-labeled antibody fragment targeted to an epitope of the antigen and a non-fluorescence-labeled intact antibody targeted to another epitope of the antigen in order to form an antigen/antibody complex among the antigen, the fluorescence-labeled antibody fragment, and the non-fluorescence-labeled intact antibody, and (ii) detecting and analyzing the formed antigen/antibody complex by fluorescence correlation spectroscopy.

2. The method of quickly detecting and/or assaying an antigen by fluorescence correlation spectroscopy according to paragraph 1, wherein the antigen is an antigenic protein.

3. The method of quickly detecting and/or assaying an antigen by fluorescence correlation spectroscopy according to paragraph 1 or 2, wherein the detection and analysis of the formed antigen/antibody complex by fluorescence correlation spectroscopy are a detection and an analysis of an antigen utilizing discrimination on the basis of a difference in diffusion rate between the fluorescence-labeled antibody fragment and the formed antigen/antibody complex that has been labeled.

4. The method of quickly detecting and/or assaying an antigen by fluorescence correlation spectroscopy according to any one of paragraphs 1 to 3, wherein the quick detection and/or assay of an antigen are a detection and/or assay of the presence, concentration, size, or shape of an antigen on the basis of detection and analysis of the formed antigen/antibody complex by fluorescence correlation spectroscopy.

5. The method of quickly detecting and/or assaying an antigen by fluorescence correlation spectroscopy according to any one of paragraphs 1 to 4, wherein the fluorescence-labeled antibody fragment targeted to an epitope of the antigen is prepared from a monoclonal antibody prepared with an antigen as an immunogen, and the non-fluorescence-labeled intact antibody targeted to another epitope of the antigen is a monoclonal antibody prepared with an antigen as an immunogen.

6. A method of quickly detecting and/or assaying an antigen by fluorescence correlation spectroscopy, comprising (i) adding a fluorescence-labeled antibody fragment targeted to an epitope of an antigen and a non-fluorescence-labeled intact antibody targeted to another epitope of an antigen to a test sample, (ii) performing antigen/antibody reaction there among, and (iii) detecting and analyzing an antigen/antibody complex formed among the antigen, the fluorescence-labeled antibody fragment, and the non-fluorescence-labeled intact antibody by fluorescence correlation spectroscopy.

7. The method of quickly detecting and/or assaying an antigen by fluorescence correlation spectroscopy according to paragraph 6, wherein the antigen is an antigenic protein.

8. The method of quickly detecting and/or assaying an antigen by fluorescence correlation spectroscopy according to paragraph 6 or 7, wherein the detection and/or assay of an antigen y fluorescence correlation spectroscopy are performed without undergoing a step of physically separating the antigen contained in the test sample.

9. The method of quickly detecting and/or assaying an antigen by fluorescence correlation spectroscopy according to any one of paragraphs 6 to 8, wherein the step of adding a fluorescence-labeled antibody fragment targeted to an epitope of the antigen and a non-fluorescence-labeled intact antibody targeted to another epitope of the antigen to a test sample, the step of performing antigen/antibody reaction among the test sample, the fluorescence-labeled antibody fragment, and the non-fluorescence-labeled intact antibody, and the step of detecting and analyzing the test sample that has undergone the antigen/antibody reaction by fluorescence correlation spectroscopy are performed automatically or semi-automatically.

10. The method of quickly detecting and/or assaying an antigen by fluorescence correlation spectroscopy according to any one of paragraphs 6 to 9, wherein the test sample is a biological protein sample, and the antigen is a pathogenic protein antigen.

11. The method of quickly detecting and/or assaying an antigen by fluorescence correlation spectroscopy according to paragraph 10, wherein the pathogenic protein antigen is an abnormal prion.

12. The method of quickly detecting and/or assaying an antigen by fluorescence correlation spectroscopy according to any one of paragraphs 6 to 9, wherein the test sample is a food material, and the antigen is a harmful protein antigen contained in the food material.

13. A detection reagent for quickly detecting and/or assaying an antigen by fluorescence correlation spectroscopy, comprising a fluorescence-labeled antibody fragment targeted to an epitope of an antigen to be detected and/or assayed and a non-fluorescence-labeled intact antibody targeted to another epitope of an antigen to be detected and/or assayed.

14. A kit for quickly detecting and/or assaying an antigen by fluorescence correlation spectroscopy, comprising a detection reagent according to paragraph 12 or 13.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of detecting and/or assaying an antigen by fluorescence correlation spectroscopy, comprising (i) adding a fluorescence-labeled antibody fragment targeted to an epitope of the antigen and a non-fluorescence-labeled intact antibody targeted to another epitope of the antigen to a test sample comprising the antigen, (ii) performing antigen/antibody reaction thereamong, and (iii) detecting and analyzing an antigen/antibody complex formed among the antigen, the fluorescence-labeled antibody fragment, and the non-fluorescence-labeled intact antibody by fluorescence correlation spectroscopy.

2. The method of detecting and/or assaying an antigen by fluorescence correlation spectroscopy according to claim 1, wherein the antigen is an antigenic protein.

3. The method of detecting and/or assaying an antigen by fluorescence correlation spectroscopy according to claim 1, wherein the detection and analysis of the formed antigen/antibody complex by fluorescence correlation spectroscopy is based on a difference in diffusion rate between the fluorescence-labeled antibody fragment and the formed antigen/antibody complex that has been labeled.

4. The method of detecting and/or assaying an antigen by fluorescence correlation spectroscopy according to claim 1, wherein the detection and analysis of the formed antigen/antibody complex by fluorescence correlation spectroscopy determines the presence, concentration, size, or shape of the antigen.

5. The method of detecting and/or assaying an antigen by fluorescence correlation spectroscopy according to claim 1, wherein the fluorescence-labeled antibody fragment targeted to an epitope of the antigen is developed from a monoclonal antibody prepared with an antigen as an immunogen, and the non-fluorescence-labeled intact antibody targeted to another epitope of the antigen is a monoclonal antibody prepared with an antigen as an immunogen.

6. The method of detecting and/or assaying an antigen by fluorescence correlation spectroscopy according to claim 1, wherein the detection and/or assay of an antigen by fluorescence correlation spectroscopy are performed without undergoing a step of physically separating the antigen contained in the test sample.

7. The method of detecting and/or assaying an antigen by fluorescence correlation spectroscopy according to claim 1, wherein steps (i), (ii), and (iii) are performed automatically or semi-automatically.

8. The method of detecting and/or assaying an antigen by fluorescence correlation spectroscopy according to claim 1, wherein the test sample is a biological protein sample, and the antigen is a pathogenic protein antigen.

9. The method of detecting and/or assaying an antigen by fluorescence correlation spectroscopy according to claim 8, wherein the pathogenic protein antigen is an abnormal prion.

10. The method of detecting and/or assaying an antigen by fluorescence correlation spectroscopy according to claim 1, wherein the test sample is a food material, and the antigen is a protein antigen contained in the food material.

* * * * *